United States Patent [19]

Ogata

[11] 4,430,331
[45] Feb. 7, 1984

[54] ANTIARRHYTMIC BENZYLIMIDAZOLE
[75] Inventor: Masaru Ogata, Osaka, Japan
[73] Assignee: Shionogi & Co., Ltd., Osaka, Japan
[21] Appl. No.: 372,951
[22] Filed: Apr. 29, 1982
[30] Foreign Application Priority Data
 May 14, 1981 [JP] Japan .................... 56-72986
[51] Int. Cl.$^3$ ............... A61K 31/415; C07D 233/90; C07D 233/60
[52] U.S. Cl. .................... 424/273 R; 424/248.55; 424/248.58; 424/250; 424/267; 424/273 B; 544/139; 544/370; 546/210; 548/325; 548/327; 548/335; 548/336; 548/343
[58] Field of Search ............. 548/335, 336, 325, 327, 548/343; 544/139, 370; 546/210; 424/273 R, 273 B, 267, 250, 248.55, 248.58

[56] References Cited
U.S. PATENT DOCUMENTS
3,870,726 3/1975 Jager et al. .................... 548/335

OTHER PUBLICATIONS
March, J., *Advanced Organic Chemistry*, McGraw Hill, New York, 1968, p. 334.

*Primary Examiner*—Richard A. Schwartz
*Attorney, Agent, or Firm*—Birch, Stewart, Kolasch & Birch

[57] ABSTRACT

Benzylazole derivatives being useful as antiarrhythmic agent are obtained by reacting the corresponding 2,3-epoxypropyloxybenzylazole with a primary or secondary amine.

11 Claims, No Drawings

ANTIARRHYTMIC BENZYLIMIDAZOLE

The present invention relates to benzylazole derivatives being useful as antiarrhythmics.

The benzylazole derivatives are represented by the formula:

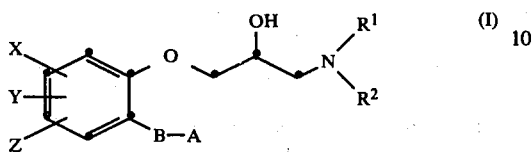

(wherein
- A is a 5- or 6-membered unsaturated heterocycle containing 1-3 nitrogen atoms or a benzimidazolyl optionally each substituted by 1-3 substituents selected from oxo, $C_1$-$C_4$ alkyl, $C_1$-$C_4$ alkoxy, $C_2$-$C_6$ alkoxycarbonyl and halogen;
- B is >CHR$^3$ or >C=CR$^4$R$^5$ in which R$^3$, R$^4$ and R$^5$ are independently hydrogen or $C_1$-$C_4$ alkyl;
- R$^1$ is $C_1$-$C_4$ alkyl;
- R$^2$ is hydrogen or $C_1$-$C_4$ alkyl; or

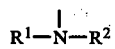

is pyrrolidinyl, piperidino, piperazino or morpholino; and
- X, Y and Z are independently hydrogen, $C_1$-$C_4$ alkyl, $C_1$-$C_4$ alkoxy or halogen)

and pharmaceutically acceptable acid addition salts thereof are included in the present invention.

The terms used in the above definition are illustratively exemplified below:
- $C_1$-$C_4$ alkyl includes methyl, ethyl, propyl, i-propyl, butyl, i-butyl, s-butyl, t-butyl;
- $C_1$-$C_4$ alkoxy includes methoxy, ethoxy, propoxy, i-propoxy, butoxy, i-butoxy;
- $C_2$-$C_6$ alkoxycarbonyl includes methoxycarbonyl, ethoxycarbonyl, propoxycarbonyl, butoxycarbonyl, pentyloxycarbonyl;
- halogen includes fluorine, chlorine, bromine, iodine; the 5- or 6-membered unsaturated heterocycle containing 1-3 nitrogen atoms includes pyrrole, imidazole, triazole, pyridine, pyridazine, pyrimidine, pyrazine, triazine, on which 1-3 substituents selected from oxo, $C_1$-$C_4$ alkyl, $C_2$-$C_6$ alkoxycarbonyl and halogen may optionally exist.

The pharmaceutically acceptable acid addition salts of Compounds I illustratively include salts with inorganic acids such as sulfuric acid, hydrochloric acid, hydrobromic acid or phosphoric acid and those with organic acids such as acetic acid, citric acid, maleic acid, malic acid, succinic acid, tartaric acid, cinnamic acid, benzoic acid, methanesulfonic acid or ascorbic acid.

Compound I is prepared by the following reaction scheme:

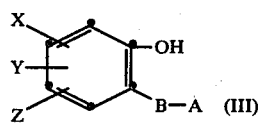

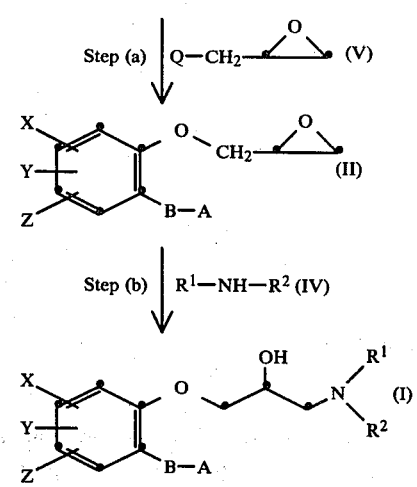

(wherein A, B, R$^1$, R$^2$, X, Y and Z have the same significance as given earlier; and Q is halogen (e.g. chlorine, bromine, iodine) or leaving group (e.g. tosyloxy)).

Accordingly Compound I is prepared by reacting the phenol derivative (III) with an epihalohydrin or 2,3-epoxypropyl ester (V) and reacting the resulting epoxide (II) with a primary or secondary amine (IV). Above steps are explained in detail below:

Step (a)

The phenol derivative (III) is reacted with an epihalohydrin (e.g. epibromohydrin, epichlorohydrin) or 1,2-epoxypropyl ester (e.g. 2,3-epoxypropyl tosylate) (V) in the presence of a base such as alkali hydroxide, alkali hydrogencarbonate, alkali carbonate, alkali alkoxide or alkali hydride in an appropriate solvent such as methanol, ethanol, benzene, toluene, dimethylformamide, dimethylsulfoxide at room temperature to the boiling point of the solvent used (e.g. 15° to 120° C.).

Step (b)

The resulting epoxide (II) is reacted with a primary or secondary amine (IV) such as methylamine, ethylamine, i-propylamine, butylamine, i-butylamine, s-butylamine, t-butylamine, dimethylamine, methylethylamine, diethylamine, dipropylamine, di-i-propylamine, methylbutylamine, methyl-i-butylamine, or ethylbutylamine in the presence or absence of an appropriate solvent such as alcohols (e.g. methanol, ethanol), ethers (e.g. ether, tetrahydrofuran), or hydrocarbons (e.g. benzene, toluene, xylene) at room temperature to the boiling point of the solvent used (e.g. about 25° to about 100° C.). In general, an excessive amount of the amine (IV) may play a role of the solvent.

The starting phenol (III) is prepared according to the following scheme:

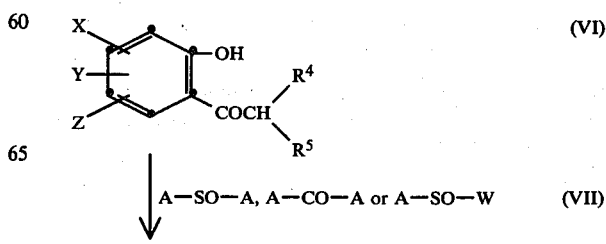

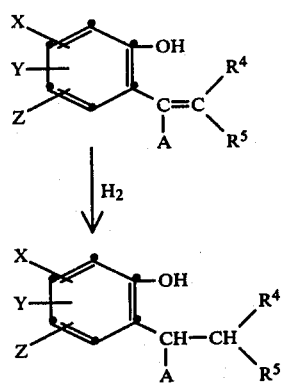

wherein W is halogen (e.g. chlorine, bromine, iodine) and A, $R^4$, $R^5$, X, Y and Z have the same significance as given earlier.

At first Compound IIIa is prepared by reacting an acetophenone derivative (VI) with a thionyl or carbonyl compound (VII) in an appropriate solvent (e.g. methylene chloride, 1,2-dichloroethane, dimethylsulfoxide, acetonitrile, dimethylformamide) at room temperature or under cooling or heating, preferably at 10° to 60° C. For example, 2-[1-(1-imidazolyl)vinyl]phenol is disclosed by Ogata et al. [Tetrahydron Letters, 52, 5011 (1979)] and 2-[1-(1-benzimidazolyl)vinyl]phenol is disclosed by Ogata et al. [Synthetic Communications, 10 (7), 559 (1980)].

Then Compound IIIb in which B is alkylene is prepared by hydrogenating Compound IIIa in a conventional manner.

Another starting compound (IIIc) is prepared as follows:

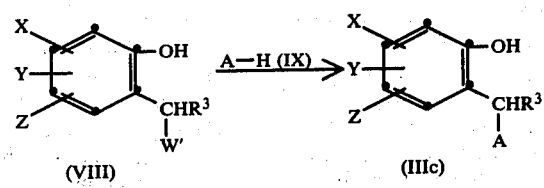

(wherein W' is a reactive group such as halogen or ester moiety (e.g. tosyloxy); and A, X, Y and Z have the same significance as given earlier). Thus the reaction of Compound VIII with Compound IX is performed in an appropriate solvent (e.g. dimethylformamide, benzene, chloroform, tetrahydrofuran, diglyme, dimethylsulfoxide) in the presence of a base such as triethylamine, pyridine, sodium amide, sodium ethoxide, or sodium hydride at room temperature to the boiling point of the solvent used. For example, o-(1-imidazolyl)methylphenol is disclosed in Japanese Unexamined Patent Publication No. 164677/1980.

A preferred compound of Compound I is shown by the formula:

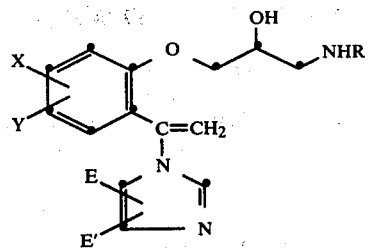

(wherein
E and E' are independently hydrogen, $C_1$-$C_2$ alkyl or $C_2$-$C_3$ alkoxycarbonyl;
R is $C_3$-$C_4$ alkyl; and
X and Y are independently hydrogen, methyl, methoxy or chlorine).

Compound I thus obtained and its pharmaceutically acceptable acid addition salts show excellent antiarrhythmic activity. Results of the pharmacological tests are shown below:

1. TEST METHOD (a) Antiarrhythmic activity (cardiomuscular action to the maximal stimulus frequency)

A certain number of atrium dextrum specimens were made by extracting the heart from male and female guinea-pigs weighing on average 350 to 600 g, and then suspended and fixed in a glass vessel filled with Krebs-Ringer-sodium carbonate solution (30° C.) in which a mixture of 95% oxygen and 5% carbon dioxide was continuously introduced. The automatism of the specimens was recorded on the oscillograph. Maximal stimulus frequency was confirmed by affording a stimulus of the atrium dextrum from the exciting electrode equipped to a retainer.

After previously treating with a test compound for 10 minutes, the reducing percent (%) of the maximal stimulus frequency was calculated by observing the reduction of the maximal frequency [Dawes, G. S.: Brit. J. Pharmacl., 1, 90 (1946)].

(b) Acute toxicity

Lethal dose was obtained by administering a test compound in the form of a physiological brine solution into the tail venae of SLC-DDY male mice weighing from 25 to 35 g and calculating the value of $LD_{50}$ by the up and down method [Brownlee, K. A. et al.: J. Am. Stat. As., 48, 262 (1953)].

2. RESULT

Table 1 shows the result of the tests, but Test Compound No. corresponds to Example No. in which the compound is prepared.

TABLE 1

| Test Compound No. | Reducing percent (%) of Maximal stimulus frequency | Acute toxicity (mg/kg) |
|---|---|---|
| 7 | 38.1 | 19.8 |
| 13 | 34.5 | 15.5 |
| 17 | 31.7 | 36.4 |
| 22 | 35.8 | 26.5 |
| 24 | 36.1 | 36.4 |
| 25 | 39.2 | 22.3 |
| 26 | 35.8 | 33.9 |
| 29 | 29.0 | 30.0 |
| 30 | 50.6 | 28.5 |
| 31 | 42.8 | 36.4 |

TABLE 1-continued

| Test Compound No. | Reducing percent (%) of Maximal stimulus frequency | Acute toxicity (mg/kg) |
|---|---|---|
| Quinidine | 22.8 | 53.6 |

As clearly shown from the above test results, Compound I obtained in the present invention shows excellent antiarrhythmia activity and is useful for treating arrhythmia or prophylaxis of angina pectoris. Further Compound I is available for treating thrombosis or the like diseases, showing platelet aggregation inhibitory activity.

Compound I may be administered enterally or parenterally and formulated in combination with appropriate carriers, diluents, and/or excipients. Customary formulations such as powders, granules, tablets, or capsules for oral administration may be prepared in combination with pharmaceutically acceptable diluents, carriers and/or excipients such as lactose, sucrose, starch, cellulose, talc, magnesium stearate, magnesium oxide, calcium sulfate, gum arabic, gelatin, sodium arginate, sodium benzoate or stearic acid. Injections may be prepared in combination with distilled water, physiological brine or Ringer solution. Appropriate dosage of Compound I to human adults is daily about 5 to about 500 mg per os and about 20 to about 400 mg at one time for intravenous administration.

Presently-preferred and practical embodiments of the present invention are illustratively shown in the following examples.

EXAMPLE 1

1-{2,4-Dichloro-6-[1-(1-imidazolyl)vinyl]phenoxy}-3-isopropylamino-2-propanol

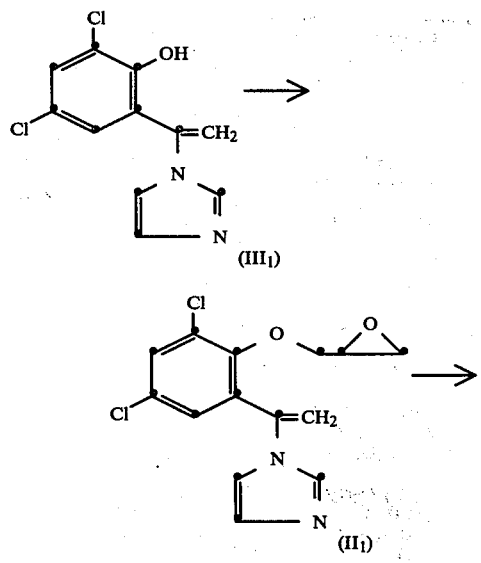

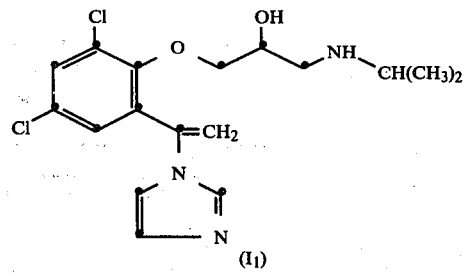

2,4-Dichloro-6-[1-(1-imidazolyl)vinyl]phenol (III$_1$) (3.9 g) is dissolved in dry dimethylformamide (47 ml), to which 5% sodium hydride (1.10 g) is added and then a solution of epibromohydrin (3.14 g) in dry dimethylformamide (2 ml) is added dropwise. The solution is stirred at 60° C. for 1.5 hours, then poured into water and extracted with benzene. The extract is washed with water, dried over sodium sulfate and evaporated to remove the benzene. Oily residue (II$_1$) is mixed with isopropylamine (20 ml), stirred at 50° C. for 19 hours and evaporated to remove the isopropylamine. To the residue is added water and sodium hydrogencarbonate and then the mixture is extracted with methylene chloride. The extract is washed with water, dried over sodium sulfate and evaporated to remove the solvent. The residue is chromatographed on alumina (Activity II). The fractions eluted with 2-3% methanol-methylene chloride are collected and evaporated to remove the solvent. The residue is washed with etherisopropyl ether and filtered to give the title compound (2.1 g) as colorless prisms, mp, 88°-90° C. Recrystallization from ethyl acetate-isopropyl ether gives colorless prisms (1.78 g), mp, 88.5°-90° C.

Anal. Calcd. for $C_{17}H_{21}O_2N_3Cl_2$: Calcd.: C, 55.14; H, 5.72; N, 11.35; Cl, 19.15; Found: C, 55.31; H, 5.67; N, 11.33; Cl, 18.89.

EXAMPLES 2-48

The same procedure as in Example 1 gives Compound I in Table 2.

The abbreviations shown below have the following meanings.

Im=1-imidazolyl
Py=1-pyrazolyl
Bim=1-benzimidazolyl
Tri=1-(1,2,4-triazolyl)
Pyd=1-(4-oxo-1,4-dihydropyridyl)
Me=methyl
Et=ethyl
i-Pr=isopropyl
i-Bu=isobutyl
t-Bu=t-butyl
d=decomposition

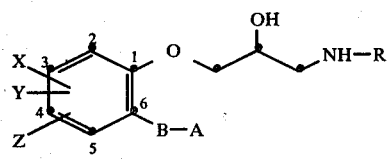

| Example | Compound I | Mp. | Molecular | Elemental Analysis |
|---|---|---|---|---|

-continued

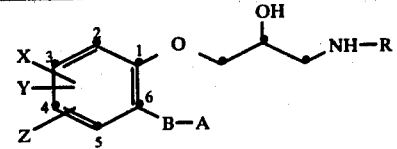

| No. | A | B | R | X | Y | Z | (°C.) | Formula | C | H | N | Cl |
|---|---|---|---|---|---|---|---|---|---|---|---|---|
| 2 | Im | C=CH$_2$ | t-Bu | H | H | H | Oil | C$_{18}$H$_{25}$O$_2$N$_3$ | 68.54 | 7.99 | 13.32 | — |
|   |    |         |      |   |   |   |     |                            | 68.31 | 8.22 | 12.85 | — |
| 3 | Im | "  | i-Pr | H | H | H | "  | C$_{17}$H$_{23}$O$_2$N$_3$·H$_2$O | 64.66 | 7.85 | 13.31 | — |
|   |    |    |      |   |   |   |    |                                   | 64.73 | 7.73 | 12.95 | — |
| 4 | Im | "  | i-Pr | 3-Cl | H | H | 79–84 | C$_{17}$H$_{22}$O$_2$N$_3$Cl·H$_2$O | 57.70 | 6.84 | 11.88 | 10.02 |
|   |    |    |      |      |   |   |       |                                       | 58.05 | 6.79 | 11.72 | 10.27 |
| 5 | Im | "  | t-Bu | 2-Cl | 4-Cl | H | 135–136.5 | C$_{18}$H$_{23}$O$_2$N$_3$Cl | 56.26 | 6.03 | 10.93 | 18.45 |
|   |    |    |      |      |      |   |            |                               | 56.26 | 6.03 | 10.91 | 18.38 |
| 6 | Im | "  | i-Pr | 4-Cl | H | H | 66.5–67.5 | C$_{17}$H$_{22}$O$_2$N$_3$Cl | 60.80 | 6.60 | 12.51 | 10.56 |
|   |    |    |      |      |   |   |            |                               | 60.85 | 6.65 | 12.39 | 10.59 |
| 7 | Im | "  | i-Pr | 2-Cl | 5-Cl | H | 117–122 | C$_{17}$H$_{21}$O$_2$N$_3$Cl$_2$ | 55.14 | 5.72 | 11.35 | 19.15 |
|   |    |    |      |      |      |   |          |                                    | 54.91 | 5.51 | 11.17 | 19.13 |
| 8 | Im | CH$_2$ | i-Pr | H | H | H | 147.5(d) | C$_{18}$H$_{25}$O$_6$N$_3$·½H$_2$O | 50.20 | 5.90 | 8.78 | — |
|   |    |        |      |   |   |   |          |                                     | 50.21 | 6.03 | 8.83 | — |

| Example No. | Compound I | | | | | | Mp | Molecular | Elemental Analysis | | | |
|---|---|---|---|---|---|---|---|---|---|---|---|---|
|   | A | B | R | X | Y | Z | (°C.) | Formula | C | H | N | Cl |
| 9 | Im | C=CH$_2$ | Me | 3-Cl | H | H | Oil | C$_{15}$H$_{18}$O$_2$N$_3$·1/6 CH$_2$Cl$_2$ | 56.58 | 5.74 | 13.05 | 14.68 |
|   |    |           |    |      |   |   |     |                                                | 56.05 | 5.62 | 12.55 | 15.20 |
| 10 | Im | C=C(Me)$_2$ | i-Pr | 4-Cl | H | H | 85–87 | C$_{19}$H$_{26}$O$_2$N$_3$Cl | 62.71 | 7.20 | 11.55 | 9.74 |
|    |    |               |      |      |   |   |       |                                | 62.70 | 7.33 | 11.31 | 9.75 |
| 11 | Im | C=CHMe | i-Pr | H | H | H | Oil | C$_{18}$H$_{25}$O$_2$N$_3$·1/5 H$_2$O | 67.77 | 8.03 | 13.17 | — |
|    |    |          |      |   |   |   |     |                                         | 68.09 | 8.12 | 12.69 | — |
| 12 | Im | " | t-Bu | H | H | H | " | C$_{19}$H$_{27}$O$_2$N$_3$·1/5 H$_2$O | 68.53 | 8.29 | 12.62 | — |
|    |    |   |      |   |   |   |   |                                         | 68.88 | 8.45 | 12.21 | — |
| 13 | Im | C=CH$_2$ | i-Bu | 2-Cl | 5-Cl | H | 104–105.5 | C$_{18}$H$_{23}$O$_2$N$_3$Cl$_2$ | 56.26 | 6.03 | 10.93 | 18.45 |
|    |    |           |      |      |      |   |            |                                    | 56.44 | 5.98 | 10.92 | 18.44 |
| 14 | Im | " | t-Bu | 2-Cl | 5-Cl | H | 147.5–149.5 | C$_{18}$H$_{23}$O$_2$N$_3$Cl$_2$ | 56.26 | 6.03 | 10.93 | 18.45 |
|    |    |   |      |      |      |   |              |                                    | 56.27 | 6.03 | 10.62 | 18.29 |
| 15 | Py | " | i-Pr | H | H | H | 66.5–67.5 | C$_{17}$H$_{23}$O$_2$N | 67.75 | 7.69 | 13.94 | — |
|    |    |   |      |   |   |   |            |                         | 67.78 | 7.92 | 14.03 | — |
| 16 | Py | " | i-Pr | 4-Cl | H | H | 131–132 | C$_{17}$H$_{22}$O$_2$N$_3$Cl (COOH)$_2$ | 53.59 | 5.68 | 9.87 | 8.32 |
|    |    |   |      |      |   |   |          |                                           | 53.33 | 5.83 | 9.81 | 8.43 |

| Example No. | Compound I | | | | | | Mp | Molecular | Elemental Analysis | | | |
|---|---|---|---|---|---|---|---|---|---|---|---|---|
|   | A | B | R | X | Y | Z | (°C.) | Formula | C | H | N | Cl |
| 17 | 4-EtOCO—5-Me—Im | " | i-Pr | H | H | H | Oil | C$_{21}$H$_{29}$O$_4$N$_3$·3/5 H$_2$O | 63.33 | 7.64 | 10.55 | — |
|    |                  |   |      |   |   |   |     |                                          | 63.65 | 7.72 | 10.18 | — |
| 18 | Im | " | i-Pr | 2-Cl | H | H | 64–66 | C$_{17}$H$_{22}$O$_2$N$_3$Cl | 60.80 | 6.60 | 12.51 | 10.56 |
|    |    |   |      |      |   |   |        |                                | 60.86 | 6.67 | 12.44 | 10.47 |
| 19 | 2-Et—5-Me—Im | " | i-Pr | H | H | H | 86.5–87 | C$_{20}$H$_{28}$O$_2$N$_3$ | 69.94 | 8.51 | 12.24 | — |
|    |               |   |      |   |   |   |          |                             | 69.93 | 8.65 | 12.17 | — |
| 20 | 2-Me—Im | " | i-Pr | H | H | H | 65–66 | C$_{18}$H$_{25}$O$_2$N$_3$·3/5 H$_2$O | 66.27 | 8.10 | 12.88 | — |
|    |          |   |      |   |   |   |        |                                         | 66.23 | 7.99 | 12.85 | — |
| 21 | Bim | " | i-Pr | H | H | H | 148–149(d) | C$_{21}$H$_{25}$O$_2$N$_3$·(COOH)$_2$·½H$_2$O | 61.32 | 6.26 | 9.33 | — |
|    |     |   |      |   |   |   |             |                                                  | 61.85 | 6.64 | 9.03 | — |
| 22 | Bim | " | t-Bu | H | H | H | 105–106 | C$_{22}$H$_{27}$O$_2$N$_3$ | 72.30 | 7.45 | 11.50 | — |
|    |     |   |      |   |   |   |          |                             | 72.40 | 7.59 | 11.26 | — |
| 23 | 2-Me—Im | " | t-Bu | H | H | H | 70–71 | C$_{19}$H$_{27}$O$_2$N$_3$ | 69.27 | 8.26 | 12.76 | — |
|    |          |   |      |   |   |   |        |                             | 69.14 | 8.46 | 12.66 | — |
| 24 | 4-Me—Im | " | i-Pr | H | H | H | Oil* | C$_{18}$H$_{25}$O$_2$N$_3$ | 68.54 | 7.99 | 13.32 | — |
|    |          |   |      |   |   |   |       |                             | 68.21 | 8.19 | 12.65 | — |
| 25 | Py | " | t-Bu | H | H | H | 75–76 | C$_{18}$H$_{25}$O$_2$N$_3$ | 68.54 | 7.99 | 13.32 | — |
|    |    |   |      |   |   |   |        |                             | 68.43 | 8.11 | 13.40 | — |
| 26 | Im | " | i-Pr | 2-Cl | 3-Cl | H | 124(d) | C$_{17}$H$_{21}$O$_2$N$_3$Cl$_2$·2(COOH)$_2$·¼ H$_2$O | 45.09 | 4.68 | 7.51 | 12.68 |
|    |    |   |      |      |      |   |         |                                                          | 45.11 | 4.57 | 7.29 | 12.33 |
| 27 | Im | " | i-Pr | 3-Cl | 5-Cl | H | Oil | C$_{17}$H$_{21}$O$_2$N$_3$Cl$_2$ | 55.14 | 5.70 | 11.35 | 19.15 |
|    |    |   |      |      |      |   |     |                                    | 54.83 | 5.73 | 10.75 | 18.96 |
| 28 | Im | " | i-Pr | 3-Cl | 4-Cl | H | " | C$_{17}$H$_{21}$O$_2$N$_3$Cl$_2$·1/5 H$_2$O | 54.61 | 5.77 | 11.23 | 18.97 |
|    |    |   |      |      |      |   |   |                                                | 54.43 | 5.83 | 10.96 | 19.01 |
| 29 | Im | " | i-Pr | 2-OMe | H | H | " | C$_{18}$H$_{25}$O$_2$N$_3$·H$_2$O | 64.84 | 8.16 | 12.60 | — |
|    |    |   |      |       |   |   |   |                                     | 64.75 | 7.92 | 12.02 | — |
| 30 | Im | " | i-Pr | 2-Cl | 5-Me | H | 126(d) | C$_{18}$H$_{24}$O$_2$N$_3$Cl·5/3 (COOH)$_2$ | 51.26 | 5.51 | 8.40 | 7.09 |
|    |    |   |      |      |      |   |         |                                                | 50.77 | 5.61 | 8.24 | 7.15 |
| 31 | Tri | " | i-Pr | H | H | H | 156–157 | C$_{16}$H$_{22}$O$_2$N$_4$·(COOH)$_2$ | 55.09 | 6.17 | 14.28 | — |
|    |     |   |      |   |   |   |          |                                          | 54.78 | 6.19 | 14.17 | — |
| 32 | Py | CH$_2$ | t-Bu | H | H | H | 177–177.5(d) | C$_{17}$H$_{25}$O$_2$N$_3$·(COOH)$_2$·1/10 H$_2$O | 57.74 | 6.94 | 10.63 | — |
|    |    |        |      |   |   |   |                |                                                      | 57.36 | 7.02 | 10.63 | — |
| 33 | Py | " | i-Pr | H | H | H | 64–65 | C$_{16}$H$_{23}$O$_2$N$_3$ | 66.41 | 8.01 | 14.52 | — |
|    |    |   |      |   |   |   |        |                             | 66.30 | 8.18 | 14.63 | — |
| 34 | Py | C=CH$_2$ | t-Bu | 4-Cl | H | H | 107–109(d) | C$_{18}$H$_{24}$O$_2$N$_3$Cl·(COOH)$_2$ | 54.61 | 5.96 | 9.55 | 8.06 |
|    |    |           |      |      |   |   |             |                                            | 54.55 | 5.98 | 9.37 | 8.04 |

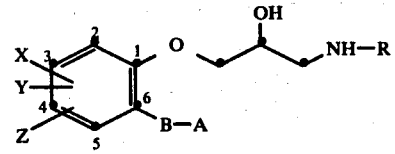

| | | | | | | | | | | | |
|---|---|---|---|---|---|---|---|---|---|---|---|
| 35 | Bim | " | i-Pr | 2-OMe | H | H | 147–148(d) | $C_{22}H_{27}O_3N_3 \cdot (COOH)_2 \cdot 1/5H_2O$ | 60.67 60.51 | 6.24 6.08 | 8.85 8.81 | — — |
| 36 | Bim | " | t-Bu | 2-OMe | H | H | 110–111 | $C_{23}H_{29}O_3N_3$ | 69.85 69.67 | 7.39 7.30 | 10.63 10.55 | — — |
| 37 | Im | " | t-Bu | 2-Cl | 5-Me | H | 131–132 | $C_{19}H_{26}O_2N_3Cl$ | 62.71 62.64 | 7.20 7.15 | 11.55 11.46 | 9.74 9.88 |
| 38 | Im | " | t-Bu | 2-Me | H | H | 145(d) | $C_{19}H_{27}O_2N_3 \cdot (COOH)_2 \cdot 5H_2O \cdot 1/5\ CH_3CN$ | 57.67 57.96 | 7.15 6.76 | 10.06 10.22 | — — |
| 39 | Im | " | t-Bu | 2-Me | 4-Cl | H | 76–78(d) | $C_{19}H_{26}O_2N_3Cl \cdot 2(COOH)_2$ | 50.79 50.84 | 5.56 5.82 | 7.73 7.51 | 6.52 6.78 |
| 40 | Im | " | i-Pr | 2-Me | 4-Cl | H | 123–127(d) | $C_{18}H_{24}O_2N_3Cl \cdot 2(COOH)_2 \cdot \frac{1}{2}H_2O$ | 49.03 48.78 | 5.42 5.18 | 7.80 7.51 | 6.58 6.48 |
| 41 | Im | " | i-Pr | 2-Cl | 4-Me | 5-Me | 99–100.5 | $C_{19}H_{26}O_2N_3Cl$ | 62.71 62.80 | 7.20 7.31 | 11.55 11.44 | 9.74 9.85 |
| 42 | Im | " | t-Bu | 2-Cl | 4-Me | 5-Me | 129–130 | $C_{20}H_{28}O_2N_3Cl$ | 63.57 63.51 | 7.47 7.51 | 11.12 10.91 | 9.38 9.44 |
| 43 | Im | " | t-Bu | 2-Me | 5-Me | H | 136.5–140 | $C_{20}H_{29}O_2N_3$ | 69.94 70.01 | 8.51 8.64 | 12.24 12.21 | — — |
| 44 | Im | " | i-Pr | 2-Me | 5-Me | H | 109–110 | $C_{19}H_{27}O_2N_3$ | 69.27 69.06 | 8.26 8.44 | 12.76 12.62 | — — |
| 45 | Im | " | t-Bu | 2-Me | 4-Me | H | 111–112 | $C_{20}H_{29}O_2N_3$ | 69.94 69.61 | 8.51 8.64 | 12.24 12.02 | — — |
| 46 | Im | " | i-Pr | 2-Me | 4-Me | H | 86–87 | $C_{19}H_{27}O_2N_3$ | 69.27 69.18 | 8.26 8.48 | 12.76 12.68 | — — |
| 47 | Pyd | " | i-Pr | H | H | H | 173.5–174.5(d) | $C_{19}H_{24}O_3N_2 \cdot 3/2(COOH)_2$ | 57.01 56.95 | 5.87 5.89 | 6.04 5.97 | — — |

*$2(COOH)_2 \cdot \frac{1}{2}CH_3CN$ salt mp. 59–63° C. (d)

REFERENCE 1

Preparation of 2-[1-(1-pyrazolyl)vinyl]phenol

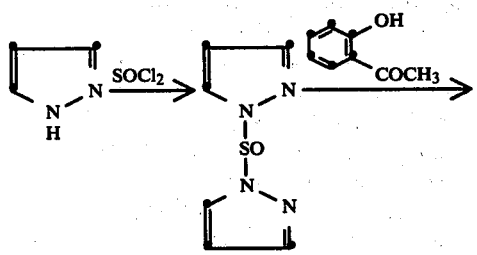

Pyrazole (9 g) is suspended in methylene chloride (45 ml), to which thionyl chloride (3.93 g) is added dropwise at 0° C. with stirring. o-Hydroxyacetophenone (3 g) is also added thereto after 10 minutes. The mixture is stirred at room temperature for 4 hours, then ice water is added thereto, and extracted with methylene chloride after being neutralized with an aqueous solution of sodium hydrogencarbonate. The extract is washed with water, dried over sodium sulfate and evaporated to remove the solvent. The residue is chromatographed on silica gel and eluted with 1-2% methanol-methylene chloride to give the title compound (198 mg). Recrystallization from ethyl acetate-petroleum ether gives crystals melting at 107.5°–109° C.

Anal. Calcd. for $C_{11}H_{10}ON_2$; Calcd.: C, 70.95; H, 5.41; N, 15.05; Found: C, 71.25; H, 5;34; N, 15.24.

The above compound is used as starting compound in Examples 15 and 25.

Starting compounds in other examples are prepared in the same manner. Melting points of new compounds are shown as follows:

| Related Example | Compound III | | | | | Mp (°C.) |
|---|---|---|---|---|---|---|
| | A | B | X | Y | Z | |
| 1,5 | Im | CH=CH₂ | 2-Cl | 4-Cl | H | 216–217 |
| 4,9 | Im | " | 3-Cl | H | H | 175–178 |
| 6 | Im | " | 4-Cl | H | H | 182–183 |
| 7,13,14 | Im | " | 2-Cl | 5-Cl | H | 182–184 |
| 10 | Im | CH=C(Me)₂ | 4-Cl | H | H | 190–194 |
| 11,12 | Im | CH=CHMe | H | H | H | 182–186.5 |
| 16,34 | Py | CH=CH₂ | 4-Cl | H | H | 140–142.5 |
| 17 | 4-EtOCO-5-Me—Im | " | H | H | H | 216–218 |
| 18 | Im | " | 2-Cl | H | H | 149–151.5 |
| 19 | 2-Et—5-Me—Im | " | H | H | H | 212–213 |
| 20,23 | 2-Me—Im | " | H | H | H | 170–172 |

-continued

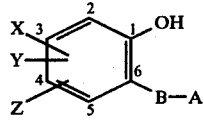

III

| Related Example | Compound III A | B | X | Y | Z | Mp (°C.) |
|---|---|---|---|---|---|---|
| 24 | 4-Me—Im | " | H | H | H | 165–170 |
| 26 | Im | " | 2-Cl | 3-Cl | H | 207–209 |
| 27 | Im | " | 3-Cl | 5-Cl | H | 193–194 |
| 28 | Im | " | 3-Cl | 4-Cl | H | 252–253.5 |
| 29 | Im | " | 2-OMe | H | H | 153–154 |
| 30,37 | Im | " | 2-Cl | 5-Me | H | 152.5–153.5 |
| 31 | Tri | " | H | H | H | 153–156 |
| 35,36 | Bim | " | 2-OMe | H | H | 192–193(d) |
| 38 | Im | " | 2-Me | H | H | 141–143 |
| 39,40 | Im | " | 2-Me | 4-Cl | H | 160–161.5 |
| 41,42 | Im | " | 2-Cl | 4-Me | 5-Me | 152–153 |
| 43,44 | Im | " | 2-Me | 5-Me | H | 130–131 |
| 45,46 | Im | " | 2-Me | 4-Me | H | 134–135 |

REFERENCE 2 o-(1-Pyrazolylmethyl)phenol

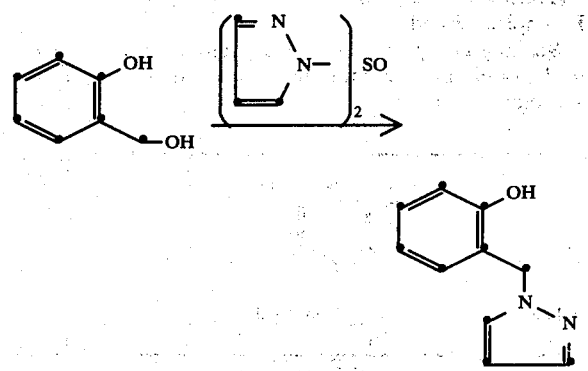

Pyrazole (24.68 g) is mixed with dry methylene chloride (123 ml), to which thionyl chloride (10.78 g) is added with stirring under ice cooling. The mixture is stirred for 10 minutes and o-hydroxybenzyl alcohol (7.5 g) is added thereto. The mixture is stirred at room temperature for 1.5 hours, then neutralized with an aqueous solution of sodium hydrogencarbonate and extracted with methylene chloride. The extract is washed with water, dried and evaporated to remove the solvent. The residue is chromatographed on silica gel. Eluates with benzene-methylene chloride are collected, evaporated to remove the solvent, washed with ethyl acetate-isopropyl ether, and filtered to give the title compound (5.95 g), mp. 123°–124° C.

Anac. Calcd. for $C_{10}H_{10}ON_2$: Calcd.: C, 68.95; H, 5.79; N, 16.08; Found: C, 69.23; H, 5.74; N, 16.11.

The above compound is used as starting compound in Examples 32 and 33.

REFERENCE 3

Preparation of 1-[1-(2-hydroxyphenyl)vinyl]4-pyridone

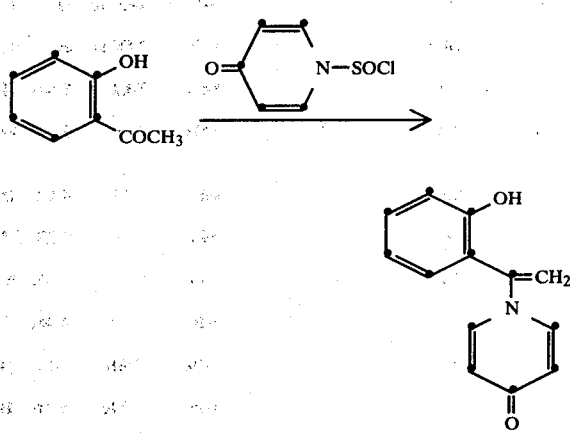

4-Hydroxypyridine (838 mg) is mixed with a mixture of triethylamine (890 mg) and dry methylene chloride (8.4 ml) and stirred under cooling. A solution of thionyl chloride (1.048 g) in methylene chloride (3 ml) is added dropwise thereto at a temperature maintained at about 10° C. and then the mixture is stirred for an additional 30 minutes and added dropwise to a mixture of o-hydroxyacetophenone (1 g), triethylamine (890 mg) and dry methylene chloride (10 ml) at the same temperature with stirring. The resultant mixture is stirred at room temperature for 15.5 hours and then ice water is added thereto. The mixture is made alkaline with sodium hydrogencarbonate and extracted with methylene chloride. The extract is washed with water, dried and evaporated to remove the solvent. The residue is chromatographed on silica gel. Eluates with 7% methanol-methylene chloride are collected and evaporated to remove the solvent. The yielded crystals are recrystallized from methanol-ethyl acetate to give the title compound (436 mg), mp. 201°–203° C.

Anal. Calcd. for $C_{13}H_{11}O_2N$: Calcd.: C, 73.22; H, 5.20; N, 6.57; Found: C, 73.17; H, 5.09; N, 6.54.

The above compound is used as a starting compound in Example 47.

EXAMPLE 48

1-{2-[1-(1-imidazolyl)vinyl]phenoxy}-3-(1-pyrrolidono)-2-propanol

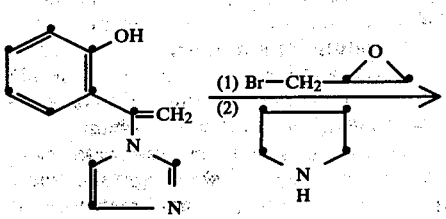

-continued

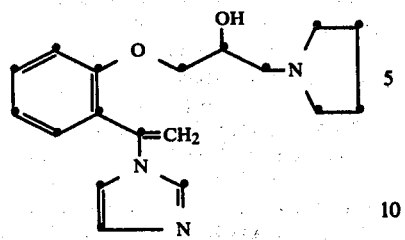

A mixture of 2-[1-(1-imidazolyl)vinyl]phenol (4 g), 50% sodium hydroxide (1.55 g), dimethyl formamide (20 ml) and epibromohydrin (4.41 g) is heated at 50° C. for 1 hour with stirring. The reaction mixture is treated in the same manner as in Example 1. The resultant epoxide is kept at room temperature for 20 hours after addition of pyrrolidine (6 ml) and then evaporated to remove the pyrrolidone. The residue is mixed with benzene and evaporated to remove the solvent. The residue is chromatographed on alumina. The eluates with 2% methanol-methylene chloride are collected and evaporated to remove the solvent. The residue is recrystallized from ethyl acetate-isopropyl ether to give the title compound (720 mg), mp. 74°–76° C.

Anal. Calcd. for $C_{18}H_{23}O_2N_3$: Calcd.: C, 68.94; H, 7.40; N, 13.41; Found: C, 69.00; H, 7.44; N, 13.37.

EXAMPLE 49

1-{2-[1-(1-imidazolyl)vinyl]phenoxy}-3-dimethylamino-2-propanol

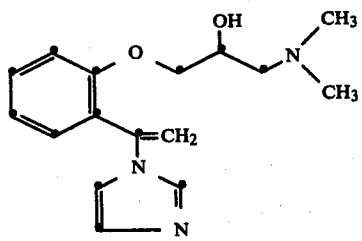

The same procedure as in Example 48 gives the title compound, mp. 62.5°–63.5° C.

Anal. Calcd. for $C_{16}H_{21}O_2N_3$: Calcd.: C, 66.87; H, 7.37; N, 14.62; Found: C, 66.73; H, 7.33; N, 14.66.

EXAMPLE 50

1-{2-[1-(1-imidazolyl)ethyl]phenoxy}-3-isopropylamino-2-propanol

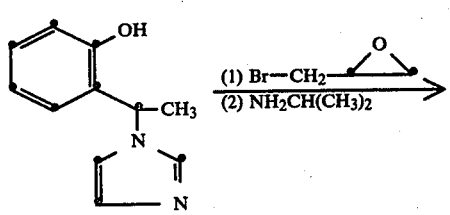

-continued

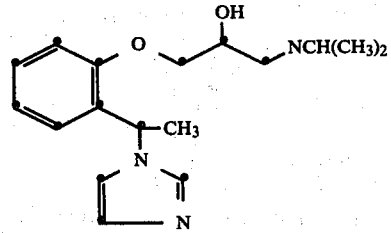

The same procedure as in Example 1 is practised with 6-[1-(1-imidazolyl)ethyl]phenol (1.0 g), 50% sodium hydride (385 mg), dehydrated dimethylformamide (10 ml) and epibromohydrin (1.10 g) to give an epoxide, which is mixed with isopropylamine (8 ml) and refluxed for 1 hour. The reaction mixture is treated in the usual manner and the resultant residue is chromatographed on alumina (activity III). The eluates with 1–3% methanol-methylene chloride are collected and evaporated to remove the solvent. The title compound (618 mg) is yielded as an oil.

Anal. Calcd. for $C_{17}H_{25}O_2N_3.3/5H_2O$; Calcd.: C, 64.98; H, 8.40; N, 13.37; Found: C, 65.22; H, 8.45; N, 12.92.

REFERENCE 4

2-[1-(1-imidazolyl)ethyl]phenol

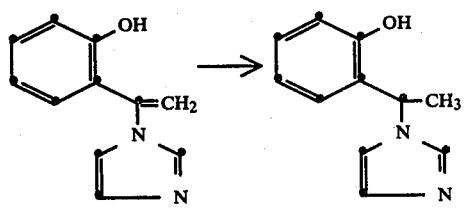

A mixture of 6-[1-(1-imidazolyl)vinyl]phenol (500 mg), methanol (20 ml), 14% hydrochloric acid-methanol (5 ml) and platinum oxide monohydrate (100 mg) is stirred in a hydrogen atmosphere and filtered when hydrogen absorption is finished, about 1.5 hours later. The filtrate is condensed, neutralized with an aqueous solution of sodium hydrogencarbonate and extracted with methylene chloride. The extract is washed with water, dried and evaporated to remove the solvent. The residue is recrystallized from ethyl acetate-isopropyl ether to give the title compound (456 mg), mp. 170.5°–172° C.

Anal. Calcd. for $C_{11}H_{12}ON_2$: Calcd.: C, 70.18; H, 6.43; N, 14.88; Found: C, 70.25; H, 6.51; N, 14.78.

The product is used as starting compound in Example 50.

What is claimed is:

1. A compound of the formula:

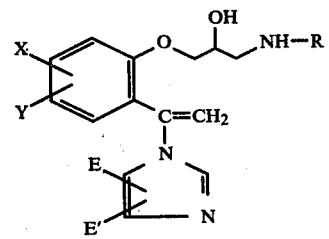

wherein
- E and E' each is hydrogen, $C_1$–$C_2$ alkyl or $C_2$–$C_3$ alkoxycarbonyl;
- R is $C_3$–$C_4$ alkyl; and
- X and Y each is hydrogen, methyl, methoxy or chlorine; or a pharmaceutically acceptable acid addition salt thereof.

2. A compound according to claim 1, namely 1-{2,5-dichloro-6-[1-(1-imidazolyl)vinyl]phenoxy}-3-isopropylamino-2-propanol.

3. A compound according to claim 1, namely 1-{2,5-dichloro-6-[1-(1-imidazolyl)vinyl]phenoxy}-3-t-butylamino-2-propanol.

4. A compound according to claim 1, namely 1-{2,5-dichloro-6-[1-(1-imidazolyl)vinyl]phenoxy}-3-isobutylamino-2-propanol.

5. A compound according to claim 1, namely 1-{2-[1-(4-ethoxycarbonyl-5-methylimidazol-1-yl)vinyl]phenoxy}-3-isopropylamino-2-propanol.

6. A compound according to claim 1, namely 1-{2-[1-(2-methyl-1-imidazolyl)vinyl]phenoxy}-3-isopropylamino-2-propanol.

7. A compound according to claim 1, namely 1-{2,3-dichloro-6-[1-(1-imidazolyl)vinyl]phenoxy}-3-isopropylamino-2-propanol.

8. A compound according to claim 1, namely 1-{2-methoxy-6-[1-(1-imidazolyl)vinyl]phenoxy}-3-isopropylamino-2-propanol.

9. A compound according to claim 1, namely 1-{2-chloro-5-methyl-6-[1-(1-imidazolyl)vinyl]phenoxy}-3-isopropylamino-2-propanol.

10. A pharmaceutical composition for treating arrhythmia comprising an antiarrhythmically effective amount of the compound claimed in claim 1 and a pharmaceutically acceptable diluent, carrier or excipient.

11. A method for treating a patient suffering from arrhythmia which comprises administering to said patient the pharmaceutical composition as claimed in claim 1.

* * * * *